US012584097B2

(12) United States Patent
De Santi Ungarato et al.

(10) Patent No.: US 12,584,097 B2
(45) Date of Patent: *Mar. 24, 2026

(54) FOAM CONTROL AGENTS FOR FERMENTATION

(71) Applicant: Dow Global Technologies LLC, Midland, MI (US)

(72) Inventors: Rafael F. De Santi Ungarato, Jundiaí (BR); Wanglin Yu, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 378 days.

This patent is subject to a terminal disclaimer.

(21) Appl. No.: 18/001,084

(22) PCT Filed: Sep. 8, 2021

(86) PCT No.: PCT/US2021/049332

§ 371 (c)(1),
(2) Date: Dec. 8, 2022

(87) PCT Pub. No.: WO2022/055906

PCT Pub. Date: Mar. 17, 2022

(65) Prior Publication Data

US 2023/0212504 A1 Jul. 6, 2023

Related U.S. Application Data

(60) Provisional application No. 63/075,397, filed on Sep. 8, 2020.

(51) Int. Cl.
*C12N 1/18* (2026.01)
*C12P 7/06* (2006.01)

(52) U.S. Cl.
CPC . *C12N 1/18* (2013.01); *C12P 7/06* (2013.01)

(58) Field of Classification Search
None
See application file for complete search history.

(56) References Cited

U.S. PATENT DOCUMENTS

| | | | | |
|---|---|---|---|---|
| 3,956,401 | A | 5/1976 | Scardera et al. | |
| 5,843,734 | A | 12/1998 | Shonaka et al. | |
| 8,357,823 | B2 * | 1/2013 | Wurm | C08G 65/2609 568/679 |
| 9,018,266 | B2 | 4/2015 | Matani et al. | |
| 9,150,886 | B2 | 10/2015 | Oliveira et al. | |
| 10,150,936 | B2 * | 12/2018 | Yu | C11D 1/722 |
| 2010/0075389 | A1 | 3/2010 | Wurm et al. | |

OTHER PUBLICATIONS

Junker, "Review Foam and Its Mitigation in Fermentation Systems"; Biotechno. Prog., 2007, pp. 767-784, vol. 23.

* cited by examiner

*Primary Examiner* — Christian L Fronda
(74) *Attorney, Agent, or Firm* — Arthur R. Rogers

(57) ABSTRACT

A fermentation method includes steps of forming a broth having yeast, water and sugar; and contacting a foam control agent with the broth, a foam formed on the broth or both, wherein the foam control agent has structure (I) wherein R is a linear or branched alkyl group containing from 4 to 18 carbon atoms, m is from 1 to 10, n is from 9 to 15, o is from 15 to 25, and o/n is from 1.00 to 2.00.

(I)

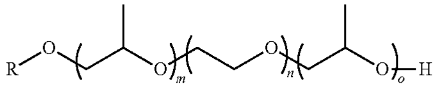

8 Claims, No Drawings

FOAM CONTROL AGENTS FOR FERMENTATION

BACKGROUND

Field of the Disclosure

The present disclosure relates to foam control agents, and more specifically, to foam control agents useful in fermentation processes.

INTRODUCTION

Ethanol production is carried out by fermenting a broth of yeast, water and sugar in a fermentation vessel. The formation of foam during fermentation is a well-known problem. The presence of proteins acting as amphiphilic agents and the large amount of $CO_2$ released during the fermentation are responsible for the foam generation. Typically, the foam at the broth-air interface is elastic in character and as such readily traps $CO_2$ rising to the surface. As the foam is resistant to dissolution, the foam accumulates as fermentation continues. Unless rigorously controlled, the foam can cause the fermentation vessel overflow, which can result in loss of broth and/or loss of ethanol.

Polyglycols are often used as foam control agents. There are two traditional approaches to the control of foam in fermentation systems including antifoaming agents and defoaming agents. Antifoaming agents are typically added directly to the broth prior to starting fermentation. Antifoaming agents operate at the broth-air interface to prevent the formation and accumulation of foam. Defoaming agents are typically applied directly to foam that has already been formed to break down the foam. Although prevention and reduction of foam are related goals, the antifoaming and defoaming agents operate in very different environments. For example, the antifoaming agent operates in the liquid broth where there are high concentrations of yeast, water, ethanol and sugars whereas the defoaming agent operates on the foam where there is a high concentration of proteins and air.

Attempts at creating a foam control agent that is both an antifoaming agent and a defoaming agent have been undertaken. For example, U.S. Pat. No. 8,357,823B2 provides an alkylene oxide capped secondary alcohol ethoxylate as a fermentation foam control agent. The secondary alcohol ethoxylate is effective as both an antifoaming agent and as defoaming agent, but relies on relatively more expensive secondary alcohols. Further, secondary alcohol foam control agents are advantaged relative to primary alcohol foam control agents due to the secondary alcohol's greater mobility from liquids to newly created interfaces (e.g., foam) compared to the primary alcohol foam control agents.

Primary alcohol-based surfactants are known for low foam cleaning applications. For example, U.S. Pat. No. 10,150,936B2 (the "'936 patent") discloses branched biodegradable low foam nonionic surfactants for use in cleaning applications. The '936 patent provides a surfactant comprising ethylene oxide ("EO") and propylene oxide ("PO") in a PO-EO-PO triblock. The '936 patent explains that the ratio of EO units to terminal PO units is desirably one or less than one in order to achieve optimal defoaming performance. The surfactant of the '936 patent is designed for use in automatic dishwashing environments (e.g., aqueous environments at temperatures from 48° C. to 65° C.).

Given the well-known unpredictability of properties based on the structure of surfactants/foam control agents and in view of the highly different structures designed for each environment outlined above, it would be surprising to discover a foam control agent comprised of a primary alcohol surfactant having a PO-EO-PO triblock structure with a terminal PO to EO ratio from 1.00 to 2.00 that can function as both an antifoaming agent and a defoaming agent for fermentation processes.

SUMMARY OF THE DISCLOSURE

The inventors of the present application have surprisingly discovered a primary alcohol surfactant having a PO-EO-PO triblock structure having a terminal PO to EO ratio from 1.0 to 2.00 that can function as both an antifoaming agent and a defoaming agent for fermentation processes. The foam control agent has structure (I):

(I)

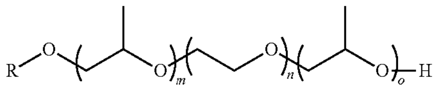

wherein R is a linear or branched alkyl group containing from 4 to 18 carbon atoms, m is from 1 to 10, n is from 9 to 15, o is from 15 to 25, and o/n is from 1.00 to 2.00. The foam control agent of the present invention is effective at functioning as an antifoaming agent by reducing foam accumulation when added to the broth and is also effective as a defoaming agent to dissipate foam after it is generated.

According to a first feature of the present disclosure, a fermentation method comprises the steps of forming a broth comprising yeast, water and sugar; and contacting a foam control agent with the broth, a foam formed on the broth or both, wherein the foam control agent has structure (I).

According to a second feature of the present disclosure, the method further comprises the step of fermenting the broth to form ethanol.

According to a third feature of the present disclosure, the o/n ratio of structure (I) is greater than 1.00.

According to a fourth feature of the present disclosure, M of structure (I) is from 3 to 7.

According to a fifth feature of the present disclosure, R of structure (I) is a branched alkyl.

According to a sixth feature of the present disclosure, a R of structure (I) is a 2-ethylhexyl moiety.

According to a seventh feature of the present disclosure, the step of contacting the foam control agent comprises contacting the foam control agent directly to the broth.

According to an eighth feature of the present disclosure, the step of contacting the foam control agent comprises contacting the foam control agent directly to the foam.

According to a ninth feature of the present disclosure, the method further comprises the step of adding a dispersing agent directly to the foam, wherein the dispersing agent comprises a glycerol-initiated or diol-initiated polymer comprising at least one of ethylene oxide and propylene oxide.

According to a tenth feature of the present disclosure, a weight ration of the dispersing agent to the foam control agent is from 0.2 to 2.5.

DETAILED DESCRIPTION

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

All ranges include endpoints unless otherwise stated.

Test methods refer to the most recent test method as of the priority date of this document unless a date is indicated with the test method number as a hyphenated two-digit number. References to test methods contain both a reference to the testing society and the test method number. Test method organizations are referenced by one of the following abbreviations: ASTM refers to ASTM International (formerly known as American Society for Testing and Materials); EN refers to European Norm; DIN refers to Deutsches Institut für Normung; and ISO refers to International Organization for Standards. When used herein, Chemical Abstract Services registration numbers refer to the most recent chemical or chemical composition designated for that registration number as of the priority date of this document.

As used herein, the term weight percent ("wt %") designates the percentage by weight a component is of a total weight of the polymeric composition unless otherwise indicated. The term mole percent ("mol %") designates the percentage by moles a component is of a total moles of the item in which the component is present.

"Polymer" means a polymeric compound prepared by polymerizing monomers, whether of the same or a different type. The generic term polymer thus embraces the terms homopolymer, interpolymer and copolymer.

Method

The present disclosure is directed to a fermentation method. The fermentation method includes a step of forming a broth comprising yeast, water and sugar and a step of contacting a foam control agent with the broth, a foam formed on the broth or both. The fermentation method may also include a step of fermenting the broth to form ethanol. Further the method may also include a step of adding a dispersing agent to the foam.

Broth

As stated above, the method includes a step of forming a broth comprising yeast, water and sugar. The sugar used in the formation of the broth may be a glucose, fructose, and/or sucrose. The sugar may be derived sugarcane, cassava, corn and/or sugar beets. At formation of the broth, the broth may comprise 5 wt % or greater, or 10 wt % or greater, or 15 wt % or greater, or 20 wt % or greater, while at the same time, 25 wt % or less, or 20 wt % or less, or 15 wt % or less, or 10 wt % or less of sugar based on the total weight of the broth. The yeast may comprise one or more of the yeast species *Saccharomyces pastorianus, Saccharomyces cerevisiae* and *Saccharomyces bayanus*. The broth may comprise 1 wt % or greater, or 2 wt % or greater, or 3 wt % or greater, or 4 wt % or greater, or 5 wt % or greater, or 6 wt % or greater, or 7 wt % or greater, or 8 wt % or greater, or 9 wt % or greater, while at the same time, 10 wt % or less, or 9 wt % or less, or 8 wt % or less, or 7 wt % or less, or 6 wt % or less, or 5 wt % or less, or 4 wt % or less, or 3 wt % or less, or 2 wt % or less of yeast based on a total weight of the broth.

As explained above, the broth may be fermented in order to form ethanol. During fermentation, the yeast converts the sugars present in the broth into ethanol and $CO_2$. The fermentation may be carried out at a temperature of from 25° C. to 36° C. and for a time period of 8 hours to 168 hours. As the $CO_2$ is released as a byproduct of the fermentation, a foam may be formed on top of the broth at a broth-air interface. The foam is characterized by a grouping of polydisperse gas bubbles separated by liquid film regions. Due to proteins and other amphiphilic agents present in the broth, the foam may resist natural dissolution into the broth. As the fermentation proceeds, the continued production of $CO_2$ may result in the accumulation of the foam.

Foam Control Agent

The fermentation method employs a foam control agent. The foam control agent has structure (I)

(I)

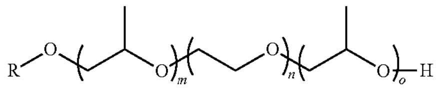

The variables "m" and "o" describe the average molar units of propylene oxide utilized in structure (I) and the variable "n" describes the average molar units of ethylene oxide in structure (I). R in structure (I) is a linear or branched alkyl group containing from 4 to 18 carbon atoms. As defined herein, R and the m, n and o values are tested and determined by Proton Nuclear Magnetic Resonance Spectroscopy and Carbon-13 Nuclear Magnetic Resonance Spectroscopy. In structure (I), m is from 1 to 10, n is from 9 to 15, o is from 15 to 25, and o/n is from 1.00 to 2.00. The m value of structure (I) is 1 or more, or 2 or more, or 3 or more, or 4 or more, or 5 or more, or 6 or more, or 7 or more, or 8 or more, or 9 or more, while at the same time, 10 or less, or 9 or less, or 8 or less, or 7 or less, or 6 or less, or 5 or less, or 4 or less, or 3 or less, or 2 or less. For example, m may be from 1 to 10, or from 4 to 9, or from 3 to 7, or from 5 to 9, or from 5 to 8, or from 5 to 7, or from 4 to 6. The n value of structure (I) is 9 or more, or 10 or more, or 11 or more, or 12 or more, or 13 or more, or 14 or more, while at the same time, 15 or less, or 14 or less, or 13 or less, or 12 or less, or 11 or less, or 10 or less. The o value of structure (I) is 15 or more, or 16 or more, or 17 or more, or 18 or more, or 19 or more, or 20 or more, or 21 or more, or 22 or more, or 23 or more, or 24 or more, while at the same time, 25 or less, or 24 or less, or 23 or less, or 22 or less, or 21 or less, or 20 or less, or 19 or less, or 18 or less, or 17 or less, or 16 or less. In a first specific example of structure (I), m 5, n 15 and o is 25. In a second specific example of structure (I), m is 5, n is 9 and o is 15. In a third specific example of structure (I), m is 5, n is 14 and o is 20.

The o/n ratio of structure (I) may be from 1.00 to 2.00. The o/n ratio of structure (I) may be greater than 1.00 to 2.00. For example, the o/n ratio may be 1.00 or greater, or 1.05 or greater, or 1.10 or greater, or 1.15 or greater, or 1.20 or greater, or 1.25 or greater, or 1.30 or greater, or 1.35 or greater, or 1.40 or greater, or 1.45 or greater, or 1.50 or greater, or 1.55 or greater, or 1.60 or greater, or 1.65 or greater, or 1.70 or greater, or 1.75 or greater, or 1.80 or greater, or 1.85 or greater, or 1.90 or greater, or 1.95 or greater, while at the same time, 2.00 or less, or 1.95 or less, or 1.90 or less, or 1.85 or less, or 1.80 or less, or 1.75 or less, or 1.70 or less, or 1.65 or less, or 1.60 or less, or 1.55 or less, or 1.50 or less, or 1.45 or less, or 1.40 or less, or 1.35 or less, or 1.30 or less, or 1.25 or less, or 1.20 or less, or 1.15 or less, or 1.10 or less, or 1.05 or less. The o/n ratio is calculated by taking the average o value divided by the average n value.

As explained above, R in structure (I) is a linear or branched alkyl group containing from 4 to 18 carbon atoms. For example, R may contain 4 carbons or more, or 5 carbons or more, or 6 carbons or more, or 7 carbons or more, or 8 carbons or more, or 9 carbons or more, or 10 carbons or more, or 11 carbons or more, or 12 carbons or more, or 13 carbons or more, or 14 carbons or more, or 15 carbons or more, or 16 carbons or more, or 17 carbons or more, while at the same time, 18 carbons or less, or 17 carbons or less, or 16 carbons or less, or 15 carbons or less, or 14 carbons or less, or 13 carbons or less, or 12 carbons or less, or 11 carbons or less, or 10 carbons or less, or 9 carbons or less, or 8 carbons or less, or 7 carbons or less, or 6 carbons or less, or 5 carbons or less. According to various examples, R is a branched alkyl. In a specific example, R is a 2-ethylhexyl ("2EH") moiety. The 2EH end group moiety can be introduced into Structure (I) by using 2-ethylhexanol as an initiator onto which the blocks of propylene oxide and ethylene oxide are polymerized. Structure (I) of the foam control agent is biodegradable.

The foam control agent is effective as both an antifoaming agent and a defoaming agent. As such, the foam control agent may be utilized in the fermentation method by contacting the foam control agent to at least one of the broth and the foam formed on the broth. Put another way, the foam control agent can be contacted with the broth, a foam formed on the broth or both. When functioning as an antifoaming agent, the step of contacting the foam control agent comprises contacting the foam control agent directly to the broth. As used herein, the terminology "directly to the broth" includes adding or contacting the foam control agent to the broth as it is being formed (i.e., mixing the foam control agent with one or more of the yeast, water, sugar and adding the other components) and or adding the foam control agent to the formed broth before or after fermentation has begun. When functioning as a defoaming agent, the foam control agent may be contacted directly to the foam. As used herein, the term "directly to the foam" includes the pouring, spraying or application of the foam control agent to foam that has formed on top of the broth. It will be understood that the foam control agent may be utilized as a neat or pure component or combined with water and/or other compounds (e.g., oils, silicones, other additives) without departing from the teachings provided herein. As explained above, the foam control agent may be used as both an antifoaming agent and a defoaming agent. As such, the foam control agent can be included in the broth before or during fermentation and then also applied direct to the foam that forms as a result of fermentation.

Dispersing Agent

The method may further include the step of adding a dispersing agent directly to the foam. The dispersing agent comprises a glycerol-initiated or diol-initiated polymer comprising at least one of ethylene oxide and propylene oxide. The diol used to initiate the dispersing agent may be an alkaline glycol such as polyethylene glycol, polypropylene glycol and/or polybutylene glycol.

The dispersing agent may comprise 5 wt % or greater, or 10 wt % or greater, or 15 wt % or greater, or 20 wt % or greater, or 25 wt % or greater, or 30 wt % or greater, or 35 wt % or greater, or 40 wt % or greater, or 45 wt % or greater, or 50 wt % or greater, or 55 wt % or greater, or 60 wt % or greater, or 65 wt % or greater, or 70 wt % or greater, or 715 wt % or greater, or 80 wt % or greater, or 85 wt % or greater, or 90 wt % or greater, or 95 wt % or greater, while at the same time, 100 wt % or less, or 95 wt % or less, or 90 wt % or less, or 85 wt % or less, or 80 wt % or less, or 75 wt % or less, or 70 wt % or less, or 65 wt % or less, or 60 wt % or less, or 55 wt % or less, or 50 wt % or less, or 45 wt % or less, or 40 wt % or less, or 35 wt % or less, or 30 wt % or less, or 25 wt % or less, or 20 wt % or less, or 15 wt % or less, or 10 wt % or less, or 5 wt % or less of ethylene oxide and/or propylene oxide. The amount of ethylene oxide and propylene oxide are tested and determined by Proton Nuclear Magnetic Resonance Spectroscopy and Carbon-13 Nuclear Magnetic Resonance Spectroscopy.

The dispersing agent mat have a weight average molecular weight of 1000 grams per mol ("g/mol") or greater, or 1500 g/mol or greater, or 2000 g/mol or greater, or 2500 g/mol or greater, or 3000 g/mol or greater, or 3500 g/mol or greater, or 4000 g/mol or greater, or 4500 g/mol or greater, or 5000 g/mol or greater, or 5500 g/mol or greater, or 6000 g/mol or greater, or 6500 g/mol or greater, or 7000 g/mol or greater, or 7500 g/mol or greater, while at the same time, 8000 g/mol or less, or 7500 g/mol or less, or 7000 g/mol or less, or 6500 g/mol or less, or 6000 g/mol or less, or 5500 g/mol or less, or 5000 g/mol or less, or 4500 g/mol or less, or 4000 g/mol or less, or 3500 g/mol or less, or 3000 g/mol or less, or 2500 g/mol or less, or 2000 g/mol or less, or 1500 g/mol or less as measured according to gel permeation chromatography.

The dispersing agent may be added to the foam such that a dispersing agent to foam control agent weight ratio is from 0.2 to 2.5 as measured by dividing the weight of dispersing agent by the weight of the foam control agent. The dispersing agent to foam control agent weight ratio may be 0.2 or greater, or 0.4 or greater, or 0.6 or greater, or 0.8 or greater, or 1.0 or greater, or 1.2 or greater, or 1.4 or greater, or 1.6 or greater, or 1.8 or greater, or 2.0 or greater, or 2.2 or greater, or 2.4 or greater, while at the same time, 2.5 or less, or 2.4 or less, or 2.2 or less, or 2.0 or less, or 1.8 or less, or 1.6 or less, or 1.4 or less, or 1.2 or less, or 1.0 or less, or 0.8 or less, or 0.6 or less, or 0.4 or less.

Use of the dispersing agent with the foam control agent may advantageously provide defoaming results greater than either agent produces singularly.

EXAMPLES

Materials

Yeast 1 is the species *Saccharomyces cerevisiae* in dehydrated form and is available under the tradename FERMEL™ from Fermentec, São Paulo, Brazil.

Yeast 2 is the species *Saccharomyces cerevisiae* in dehydrated form and is available under the tradename FLEISCHMANN'S YEAST™ from ACH Foods, Oakbrook Terrace, IL.

Sugar is refined white sucrose.

Table 1 provides the composition of the foam control agents ("FCA") and dispersing agents ("DA") used in the examples. Each of the FCA and DA may be obtained from The Dow Chemical Company, Midland, MI. In Table 3, ethylene oxide ("EO") and propylene oxide ("PO") are provide in weight percent and the diol initiator used is propylene glycol having a weight average molecular weight of from 1800 g/mol to 2000 g/mol. The provided molecular weights are weight average molecular weights as determined according by gel permeation chromatography.

TABLE 1

| Agent | Structure (I) | Molecular weight (g/mol) | o/n ratio | Initiator | EO (%) | PO (%) |
|---|---|---|---|---|---|---|
| FCA1 | R = 2EH, m = 5, n = 9, o = 5 | 1100 | 0.55 | | | |

TABLE 1-continued

| Agent | Structure (I) | Molecular weight (g/mol) | o/n ratio | Initiator | EO (%) | PO (%) |
|---|---|---|---|---|---|---|
| FCA2 | R = 2EH, m = 5, n = 15, o = 10 | 1650 | 0.67 | | | |
| FCA3 | R = 2EH, m = 5, n = 15, o = 25 | 2530 | 1.67 | | | |
| FCA4 | R = 2EH, m = 5, n = 9, o = 15 | 1690 | 1.67 | | | |
| FCA5 | R = 2EH, m = 5, n = 6, o = 3 | 860 | 0.50 | | | |
| FCA6 | R = 2EH, m = 5, n = 14, o = 20 | 2250 | 1.43 | | | |
| DA1 | | 2500 | | Diol | 27.2 | 72.8 |
| DA2 | | 3700 | | Glycerol | 26.3 | 73.7 |
| DA3 | | 4000 | | Glycerol | 13.8 | |
| DA4 | | 1800 | | Diol | 5.8 | |
| DA5 | | 1870 | | Diol | 9.7 | |

Sample Preparation

The tested yeast was hydrated in tap water at 10 wt % based on the total water and yeast weight to form a yeast dispersion. A sugar solution was formed of tap water and 20 wt % sugar based on the total weight of the tap water and sugar. 300 grams (g) of the yeast dispersion and 600 g of the sugar solution were mixed in order to produce a broth.

For antifoaming test samples, 0.135 g of the indicated foam control agent was added to the broth yielding an antifoaming sample. For defoaming test samples, 0.270 g of DA2 was added to the broth to form a defoaming sample.

Test Methods

Antifoaming Test: The total mass of the antifoaming sample was transferred to a cylindrical vessel fixed on a PERMENTEST™ fermentation test kit from Tecnal. An airflow of 7.0 liters per minute was injected from the bottom of the cylindrical vessel through a porous plate to generate foam in the sample. The time required for the foam to reach 25 centimeters ("cm") in height was recorded as a measure of foamability and foam stability of a sample. The longer the time to reach the 25 cm foam height, the better the foam control agent worked. After 300 seconds, if the foam height of a sample did not reach 25 cm, the experiment was stopped and the time was reported as 300 seconds. Foam height was measured by visually observing a scalebar present on the side of the vessel. Each experiment was repeated twice and the mean of the results are reported in Table 2.

Defoaming Test: The total mass of the defoaming sample was transferred to a cylindrical vessel fixed on a FERMENTEST™ fermentation test kit from Tecnal. An airflow of 7.0 liters per minute was injected from the bottom of the cylindrical vessel through a porous plate to generate foam in the sample. When the foam reached a height of 20 cm in the cylindrical vessel, 0.27 g of the foam control agent and/or dispersing agent was added via pipette to break the foam. The minimum height of the foam after the addition of the foam control agent and/or dispersing agent and the time it took to reach the minimum height were recorded. Each experiment was repeated twice and the mean of the results are reported in Table 3.

Antifoaming Results

Table 2 reports the antifoaming results of inventive examples ("IE") IE1-IE6 and comparative examples ("CE") CE1-CE12.

TABLE 2

| Example | Material | Yeast | Time (S) |
|---|---|---|---|
| IE1 | FCA3 | 1 | 300.0 |
| IE2 | FCA3 | 2 | 300.0 |
| IE3 | FCA4 | 1 | 300.0 |
| IE4 | FCA4 | 2 | 300.0 |
| IE5 | FCA6 | 1 | 300.0 |
| IE6 | FCA6 | 2 | 300.0 |
| CE1 | FCA1 | 1 | 59.2 |
| CE2 | FCA1 | 2 | 130.2 |
| CE3 | FCA2 | 1 | 68.1 |
| CE4 | FCA2 | 2 | 189.7 |
| CE5 | FCA5 | 1 | 115.2 |
| CE6 | FCA5 | 2 | 229.9 |
| CE7 | DA1 | 1 | 134.5 |
| CE8 | DA1 | 2 | 170.9 |
| CE9 | DA2 | 1 | 117.1 |
| CE10 | DA2 | 2 | 171.2 |
| CE11 | None | 1 | 92.0 |
| CE12 | None | 2 | 105.1 |

Three of the foam control agents prevented foam growth from reaching a height of 25 cm: FCA3, FCA4 and FCA6. Referring to the composition information in Table 1, one can find that these 3 foam control agents all have, with respect to structure (I) an n value from 9 to 15, an o value from 15 to 25, and an o/n value from 1.00 to 2.00. Each of CE1-CE10 reached the 25 cm of foam height in less than 300 seconds. When examining foam control agents of the comparative examples, the o/n value of these materials was less than 1.00 and otherwise deviated from the m, n and o values of structure (I). It is surprising that foam control agents having, with respect to structure (I), an n value from 9 to 15, an o value from 15 to 25, and an o/n value from 1.00 to 2.00 are able to effectively act as antifoaming agents while the same structure with different m, n, o and n/o values is unable to effectively function as an antifoaming agent.

Defoaming Results

Table 3 reports the antifoaming results of IE7 and IE8 and CE 13 and CE 14.

TABLE 3

| Example | Material | Yeast | Minimum Height (cm) | Time to reach minimum height (s) |
|---|---|---|---|---|
| CE13 | FCA5 | 1 | 23 | — |
| CE14 | DA3 | 1 | 11.25 | 108 |
| IE7 | FCA6 | 1 | 5.25 | 41 |
| IE8 | FCA6 + DA3 (50:50 weight ratio) | 1 | 1 | 18 |

As can be seen from Table 3, FCA5 was unable to function as a defoaming agent as the foam continued to rise from 20 cm at introduction of the foam control agent to 30 cm after 5 minutes post introduction. The structure of FCA5 (R=2EH, m=5, n=6, o=3) was therefore unable to function as either an antifoming or a defoaming agent. In contrast, FCA6 was able to break the foam and function as a defoaming agent in addition to an antifoaming agent. It is believed that FCA6 was able to function as both an antifoaming agent and a defoaming agent because FCA6 had, with respect to structure (I), an n value from 9 to 15, an o value from 15 to 25, and an o/n value from 1.00 to 2.00. It is believed that other foam control agents having an n value from 9 to 15, an o value from 15 to 25, and an o/n value from 1.00 to 2.00 (i.e., FCA3 and FCA4) would provide similar defoaming results as FCA6. DA3, while able to break the foam, was less effective as a defoaming agent than FCA6. Surprisingly, a 50:50 weight ratio of DA3 and FCA6 was able to produce results greater than either FCA6 and DA3 on its own.

What is claimed is:

1. A fermentation method, comprising the steps of:

forming a broth comprising yeast, water and sugar; and contacting a foam control agent and a dispersing agent with the broth, a foam formed on the broth or both, wherein the foam control agent has structure (I):

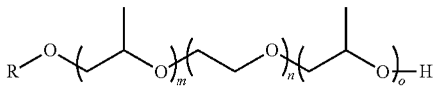

(I)

wherein R is a linear or branched alkyl group containing from 4 to 18 carbon atoms, m is from 1 to 10, n is from 9 to 15, o is from 15 to 25, and o/n is from 1.00 to 2.00, and wherein the dispersing agent comprises a glycerol-initiated or diol-initiated polymer comprising at least one of ethylene oxide and propylene oxide, wherein the weight ratio of the dispersing agent to the foam control agent is from 0.2 to 2.5.

2. The method of claim 1, further comprising the step of: fermenting the broth to form ethanol.

3. The method of claim 1, wherein the o/n ratio of structure (I) is greater than 1.00.

4. The method of claim 1, wherein M of structure (I) is from 3 to 7.

5. The method of claim 4, wherein R of structure (I) is a branched alkyl.

6. The method of claim 5, wherein R of structure (I) is a 2-ethylhexyl moiety.

7. The method of claim 1, wherein the step of contacting the foam control agent comprises contacting the foam control agent directly to the broth.

8. The method of claim 1, wherein the contacting of the foam control agent comprises contacting the foam control agent directly to the foam.

* * * * *